United States Patent [19]

Sibalis

[11] Patent Number: 4,731,926
[45] Date of Patent: Mar. 22, 1988

[54] METHOD OF MANUFACTURING DISPOSABLE AND/OR REPLENISHABLE TRANSDERMAL DRUG APPLICATORS

[75] Inventor: Dan Sibalis, Stony Brook, N.Y.

[73] Assignee: Drug Delivery Systems Inc., New York, N.Y.

[21] Appl. No.: 807,234

[22] Filed: Dec. 10, 1985

Related U.S. Application Data

[63] Continuation-in-part of Ser. No. 702,486, Feb. 19, 1985, which is a continuation-in-part of Ser. No. 660,192, Oct. 12, 1984, Pat. No. 4,622,031, which is a continuation-in-part of Ser. No. 524,252, Aug. 18, 1983, Pat. No. 4,557,723.

[51] Int. Cl.$^4$ ............................................. H01R 43/02
[52] U.S. Cl. ....................................... 29/877; 128/641; 604/20
[58] Field of Search ................. 128/640, 641, 798; 29/877, 878; 604/20

[56] References Cited

U.S. PATENT DOCUMENTS

| | | |
|---|---|---|
| 2,667,162 | 1/1954 | Zwahlen . |
| 4,063,352 | 12/1977 | Bevilacqua ................... 29/877 X |
| 4,362,645 | 12/1982 | Hof et al. . |
| 4,416,274 | 11/1983 | Jacobesen et al. ................ 604/20 |
| 4,433,481 | 2/1984 | Szpur . |
| 4,441,500 | 4/1984 | Sessions et al. . |
| 4,474,570 | 10/1984 | Ariura et al. . |
| 4,477,971 | 10/1984 | Jacobsen et al. ................. 29/877 |
| 4,557,723 | 10/1985 | Sibalis ............................. 604/20 |

FOREIGN PATENT DOCUMENTS

| | | |
|---|---|---|
| 3225748 | 4/1983 | Fed. Rep. of Germany . |
| 2104388 | 3/1983 | United Kingdom . |
| 694198 | 10/1979 | U.S.S.R. . |

Primary Examiner—Howard N. Goldberg
Assistant Examiner—Carl J. Arbes
Attorney, Agent, or Firm—Lackenbach Siegel Marzullo & Aronson

[57] ABSTRACT

Applicators for the electrophoretic and/or electroosmotic deposition of a medicament across the skin and into the blood stream. The applicator includes a plurality of drug reservoir electrodes, a battery, a plurality of folded members each having an electrically conductive coating on a flexible, non-conductive substrate in electrical contact with the batttery and the drug reservoir electrodes, electrical current conditioning means, a cover adhesively secured to the applicator, and a release liner covering and protecting the drug reservoirs until use. A method of manufacturing the applicator is set forth.

32 Claims, 12 Drawing Figures

METHOD OF MANUFACTURING DISPOSABLE AND/OR REPLENISHABLE TRANSDERMAL DRUG APPLICATORS

RELATED U.S. PATENT APPLICATIONS

This application is a continuation-in-part of U.S. patent applications, Ser. No. PCT/US85/01075 filed June 10, 1985, and Ser. No. 702,486, filed Feb. 19, 1985, which in turn is a continuation-in-part of earlier filed patent applications Ser. No. PCT/US/85/00080, filed Jan. 17, 1985; Ser. No. 660,192, filed Oct. 12, 1984 now U.S. Pat. No. 4,622,031 issued 11/11/86; and Ser. No. 524,252, filed Aug. 18, 1983 now U.S. Pat. No. 4,557,723 issued 12/10/85; all of the above-identified patent applications, as well as the instant patent application currently assigned to Drug Delivery Systems Inc.

INCORPORATION BY REFERENCE

This application incorporates by reference my earlier filings, Ser. No. PCT/US85/01075, filed June 10, 1985; and Ser. No. 702,486, filed Feb. 19, 1985, complete copies of which are attached hereto and expressly made a part of this disclosure as pages A1 through A-76 as a matter of convenience.

FIELD OF THE INVENTION

This invention relates to disposable as well as replenishable transdermal drug applicators which are electrically powered, and to methods for making such constructions. A complete electrical circuit is made through the skin once the drug applicator is adhered thereto, whereby at least one physico/chemical mass transfer phenomenon takes place causing the drug or medicament to migrate through the skin.

BACKGROUND OF THE INVENTION

Reference to or disclosure of devices for transdermal delivery of drugs by application of electrical current through the skin of a person or animal are shown in the following U.S. Pat. Nos.:

385,556
486,902
588,479
2,493,155
2,667,162
2,784,715
3,163,166
3,289,671
3,547,107
3,677,268
4,008,721
4,141,359
4,239,046
4,243,052
4,325,367
4,367,745
4,419,091
4,474,570
4,406,658
4,314,554
4,166,457
4,239,046
4,250,878
4,164,226
4,362,645
4,273,135

The following foreign Pat. Nos. refer to or disclose transdermal delivery devices:
EPA 0060452
DE 290202183
DE 3225748
EPA 0058920
UK 2104388

DESCRIPTION OF THE PREFERRED EMBODIMENTS

It should also be noted that as a convenience in the following description of the invention, like numerals are representative of similar elements common to the various embodiments of the invention.

Figure 1:
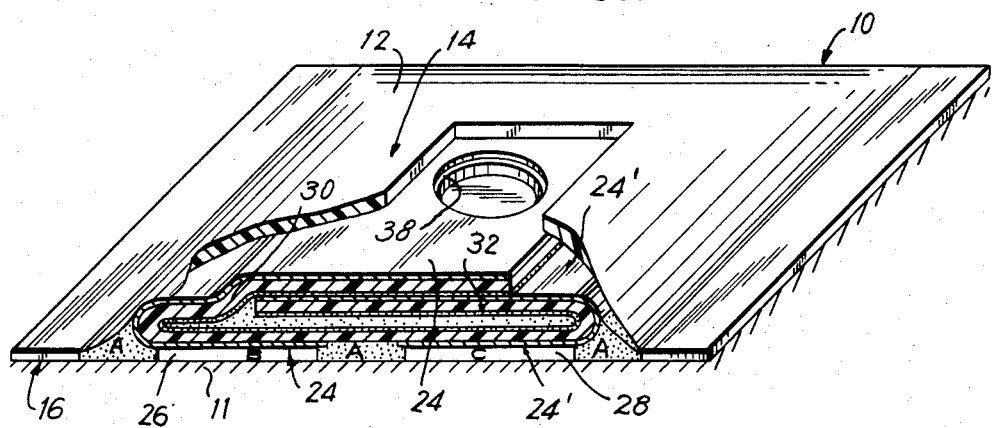
FIG. 1 is a perspective view, partially cut away, so as to illustrate the innards of a self-contained drug applicator of the invention.
Figure 2:
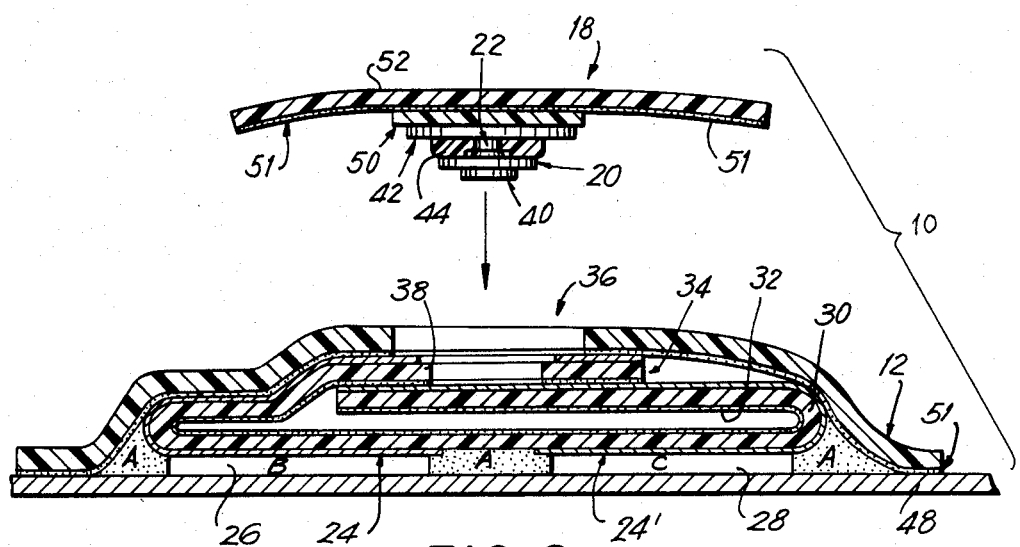
FIG. 2 is a longitudinal cross-sectional view of the drug applicator of FIG. 1, and also illustrating in exploded view a reusable power supply which may be provided with a programmable control and wrist watch mounting.

Referring now to FIGS. 1-2, there is shown a transdermal drug applicator 10 which is adhered to the skin 11 comprising an outer cover 12 with a centrally raised portion 14 and a peripheral sealed area or lip portion 16. Such an applicator is of the replaceable type having provision for connection to a reusable power supply 18 which may be, if desired, part of a wrist watch mounting having optionally a programmable control device such as more particularly described and claimed in said aforementioned earlier filed patent application, Ser. No. PCT/US85/01075, filed June 10, 1985.

Power supply 18 comprises a suitable disc battery 20 having electrodes or terminals on opposite sides thereof. One battery electrode is electrically connected to current conditioning or electronic conditioning means 22 and by means of suitable snap-on or other type of mechanical connectors (silver-plated Velcro connections manufactured by Velcro Corporation of America), or by conductive and reusable adhesives; and the battery electrodes are in turn connected to conductors 24,24' extending from drug reservoirs 26,28, which are also indicated as reservoirs B and C, respectively. The conductors 24, 24' are flexible suitably conductive surfaces or coatings on a flexible plastic substrate 30 which is non-conductive, impermeable, stable and otherwise compatible with drugs, adhesives, the skin and any other materials from which the device is fabricated. The conductive surface or coated areas may, if desired, suitably comprise a coating containing a carbonaceous material, such as carbon powder and/or graphite; and the conductive coating may further include a depolarizing agent or the conductive coated areas may comprise a noble metal. Each conductor 24, 24' with its substrate 30 forms a seamless, one-piece, folded member. When bent and folded back upon itself; the plastic substrate 30 and conductive surfaces bring the electrical contacts to the top side of the drug applicator where the electrical connections are to be made with the reusable power supply 18. The adhesive coating 32 on the inside (and topside) of the plastic substrate 30 secures together the mating surfaces as well as the overlapping edge or end 34 which is provided with a suitable slot or aperture 36 representing a nest or well area for receiving the power supply 18 and its electrical connectors. A small peripheral clearing 38 about the aperture 36 represents an insulating guard area to preclude any possibility of shorting out. Thus, the lower electrode 40 and upper electrode 42 of the battery directly or indirectly make electrical contact with conductors 24, 24'. Suitable insulating material 44 surrounds the current or electronic conditioning means 22, and suitable insulating material "A", which forms the dam separating the drug reservoirs 26, 28 and provides the end seals for not only the side of longitudinal edges but also for the transverse edges of the transdermal drug applicator. Conformable cover 12 protects the entire device and may be suitably of a skin tone or color and the like appearance.

Should snaps or other type of material fasteners be employed, it is preferable if the disposition of same is such that the snaps are not symmetrically laid out as such arrangement would ensure that the power supply could only be mated in a single manner.

With the drug applicator shown being of electrode/reservoir construction of the side by side type, the cover need not be conductive as the lip portion merely acts as a peripheral seal and not a return electrode. However, it will be appreciated that the invention is also applicable to drug applicators of the "matted" frame construction where the lip portion acts as the return or inactive electrode. In such case, then the conformable cover must also be conductive.

Electro-kinetic mass transfer processes require an electric power source, and in the case of electrophoresis an ionized drug migrates from the drug applicator patch through the skin and into the blood stream, whereas in the case of electroosmosis, a fluid carrier, such as water, is likewise transported across the skin and into the blood stream carrying along with it any and all dissolved constituents (ionized drugs or otherwise). Either or both of these two physicochemical phenomena may jointly work together or independently in transdermally carrying a drug or drugs across the skin in a desired dosage release and/or relatively steady pattern.

The application of an electric field across the skin greatly enhances the skin permeability to various drugs.

Prior to the attachment to the skin, a suitable release, liner or web, 48 is removed leaving the two drug reservoirs, insulating dam and peripheral seals free to adhere to the skin.

It should also be understood that the power supply 18 is supported by a like plastic substrate 50 which is in turn suitably adhesively secured by adhesive 51 to a small conformal cover 52 which neatly covers over and seals off the apertured area where the electrical connections are made. This ensures that the device can be worn at all times; such as in the rain or in the shower or bath.

Figure 2A:
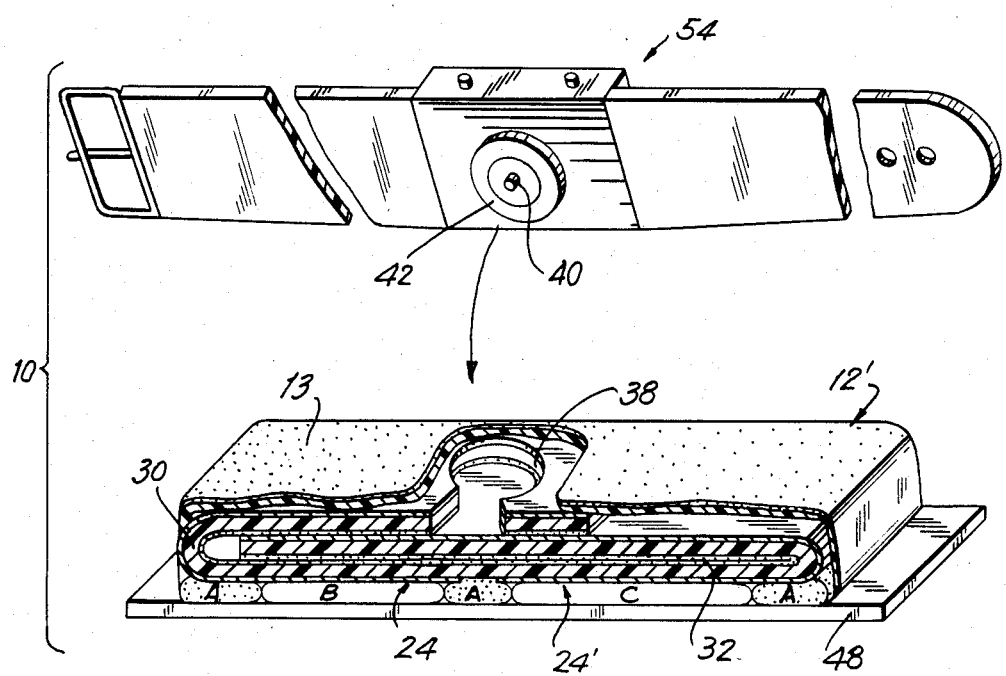
FIG. 2A is a view similar to FIG. 2, but shown perspectively, in which the power supply and the programmable control are contained within a wrist watch mounting having concentric connectors.

If desired, the reusable power supply 18 may be part of a wrist watch 54, as shown in FIG. 2A, having a programmable computer with concentric conductive adhesive connectors 40, 42, such as previously disclosed in said earlier patent filing with like electrical connections and mechanical securement being provided where needed to achieve such packaged construction. The main difference between the disposable drug applicators shown in FIGS. 2 and 2A is that the conformal cover means 12' of FIG. 2A is coated with an adhesive layer 13. Such adhesive layer 13 allows removal of the drug applicator and replacement same as adhesive 51 in FIG. 2.

Figure 3:
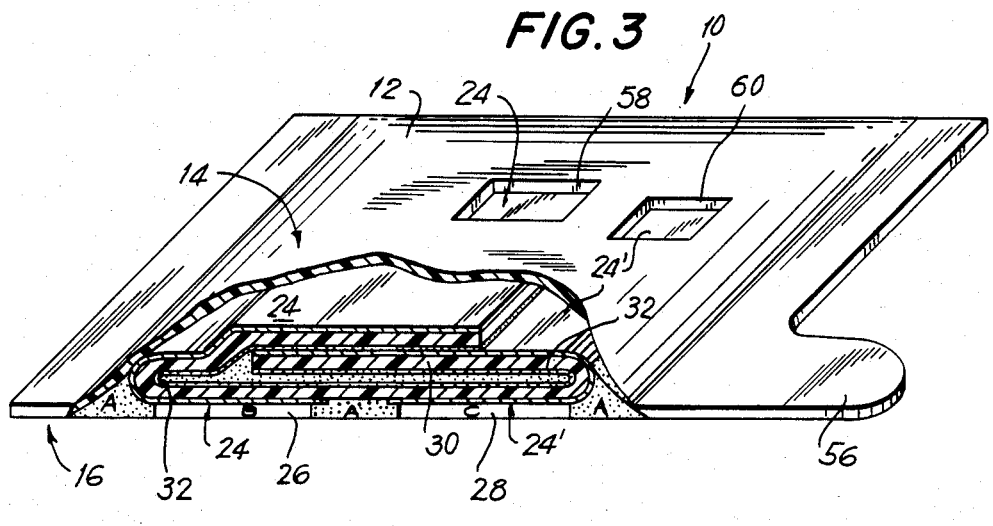
FIG. 3 is another perspective view similar to FIG. 1, but showing an alternate construction having a pair of off-center apertures or slots for the electrical connections in lieu of concentric electrical contacts made through the use of a single center aperture so as to enable the mounting of a new drug applicator to the reusable power supply in a keyed or polarized manner.

The alternate construction shown in FIG. 3 simply adds the feature of an optimal tab 56 for the release liner or paper 48, and the use of offset apertures 58 and 60 for mating with the conductive adhesive contacts at the bottom of battery 20 and the extended substrate 50 which may be offset in a manner to provide just side to side connection in lieu of concentric or symetric connections.

Figure 4:
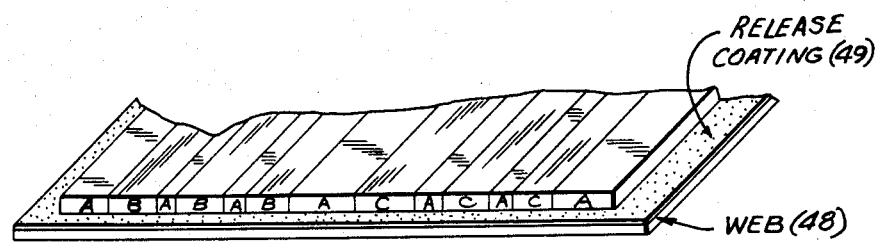
FIGS. 4 and 5 are fragmentary perspective views of typical configurations of drug electrodes/reservoirs provided on endless web substrates fed from rolled stock material, with occlusive adhesive dams separating the drug reservoirs longitudinally, as well as transversely.
Figure 5:
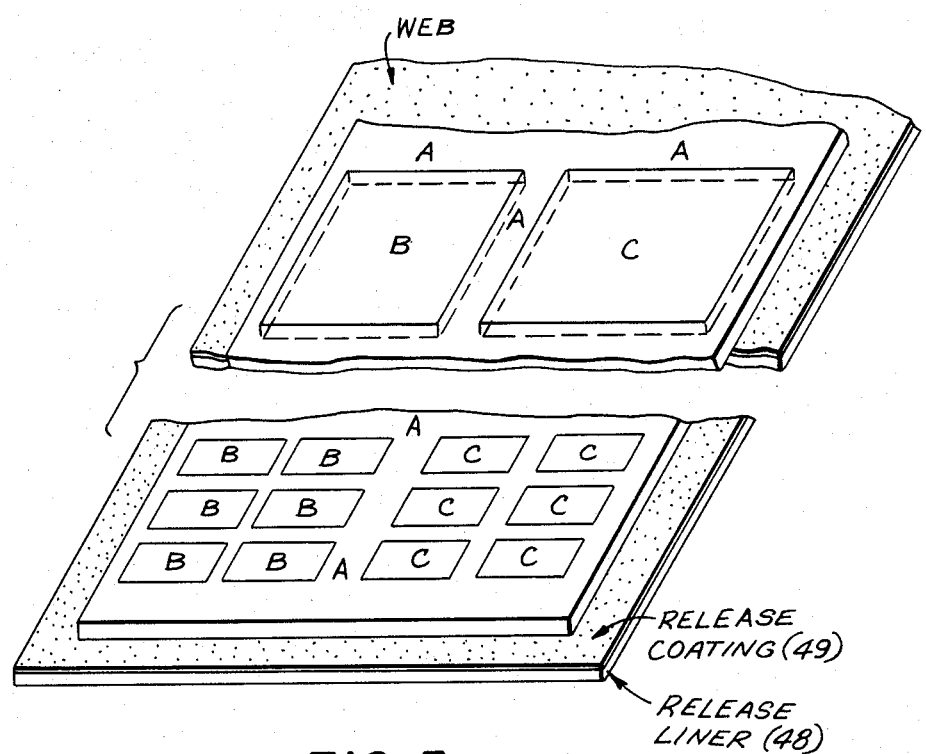
Figure 6:
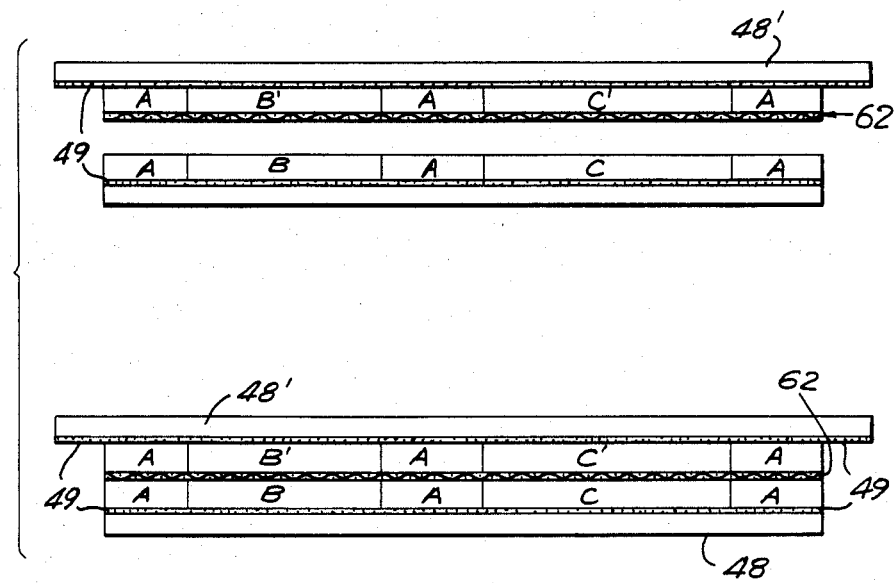
FIGS. 6 and 7 respectively illustrate diagrammatically typical assemblies of drug electrodes/reservoirs forming larger reservoir means; or forming drug gradient with layers of both high and low drug concentration within reservoirs separated by a semipermeable membrane or reinforcing scrim.
Figure 7:
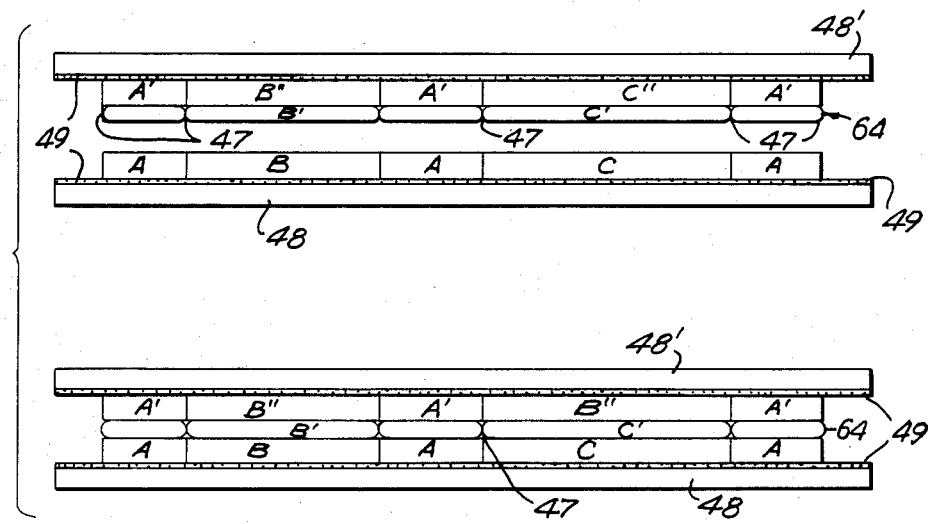
Figure 8:
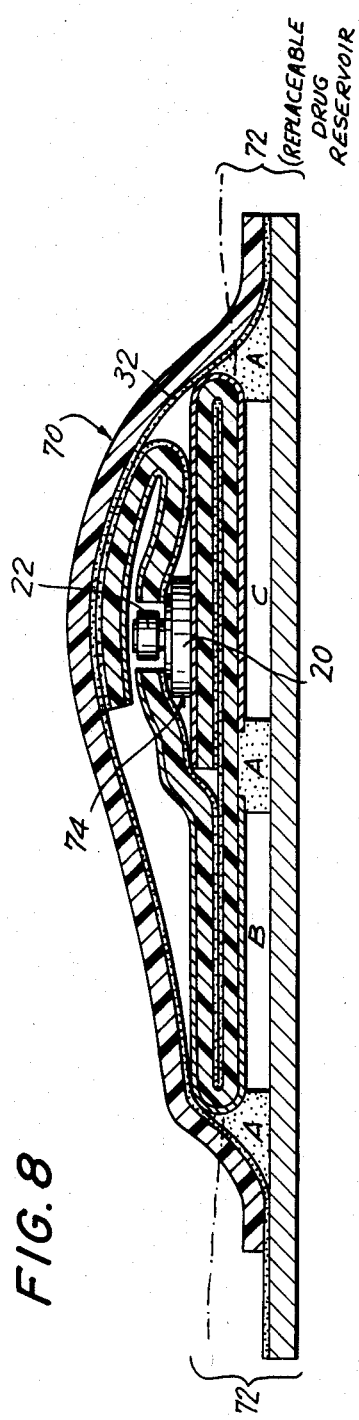
FIG. 8 is a cross-sectional view of a disposable drug applicator with a separate subassemblied power source and electrical conditioning means adhesively assembled along their electrodes to any one typical drug electrode/reservoir assemblies shown in FIGS. 6-7.
Figure 9:
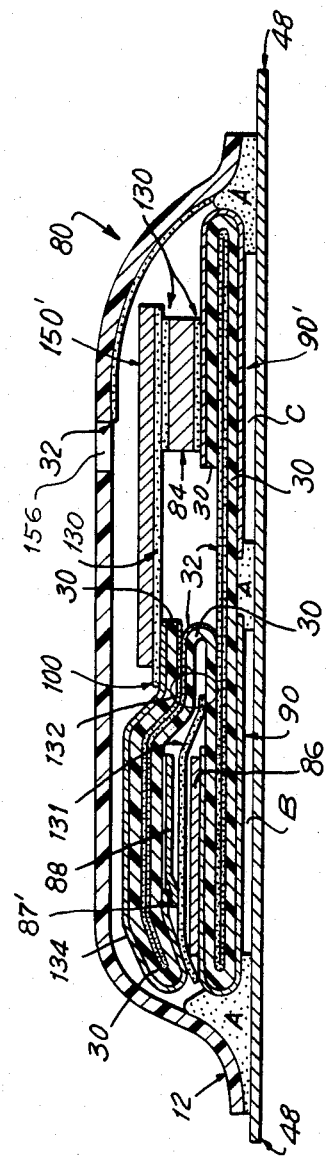
FIG. 9 is a cross-sectional view of an alternate construction having similarly optionally replaceable drug reservoirs (electrodes/reservoirs), and with flat batteries forming a sub-assembly with electrical connections to electronic conditioning means.

In FIGS. 4-7, drug sub-assemblies are illustrated for use with the disposable transdermal drug applicators shown in FIGS. 8-9. As shown in FIGS. 4 and 5, the drug reservoirs may be suitable gel layers which can be rolled or otherwise applied to a webbed substrate fed from endless rolled sheet material while being separated between reservoirs and about their extreme edges by applied occlusive adhesive dams. The dams are identified by the Letters A and the drug reservoirs are marked with the letters B representing negative and C representing positive. The "quilt" type pattern where multiple drug reservoirs are employed can be fabricated by repetitive operative steps using a silk screen printing or transfer process. It should also be recognized that the substrate is coated with a suitable release agent 49, such as silicone and when the sub-assembly is combined into a complete transdermal drug applicator or patch, the substrate in effect becomes the release liner 48, discussed previously.

FIGS. 6–7 illustrate the assembly of two drug applicator sub-assemblies. For example, in FIG. 6, an optional reinforcing web or vail-like material (scrim) 62 may be used to reinforce the gel "drug" reservoirs.

One embodiment uses an open cell foam which is impregnated in different areas with gel drug reservoirs surrounded by occlusive adhesive dam penetrating the same open cell foam. Such a structure allows the construction of a thick replaceable drug reservoir in which the gel will maintain its integrity during manufacturing, the application to and removal from human skin, as well as to the replacement of exhausted drug reservoirs. In manufacture, the open cell foam web may be suitably attached to a release liner, then provided with occlusive adhesive dams which completely penetrate the full thickness of the open cell foam, thus forming or designating the drug reservoir areas which can be subsequently filled in with their respective drug/gel mixtures.

Figure 10:
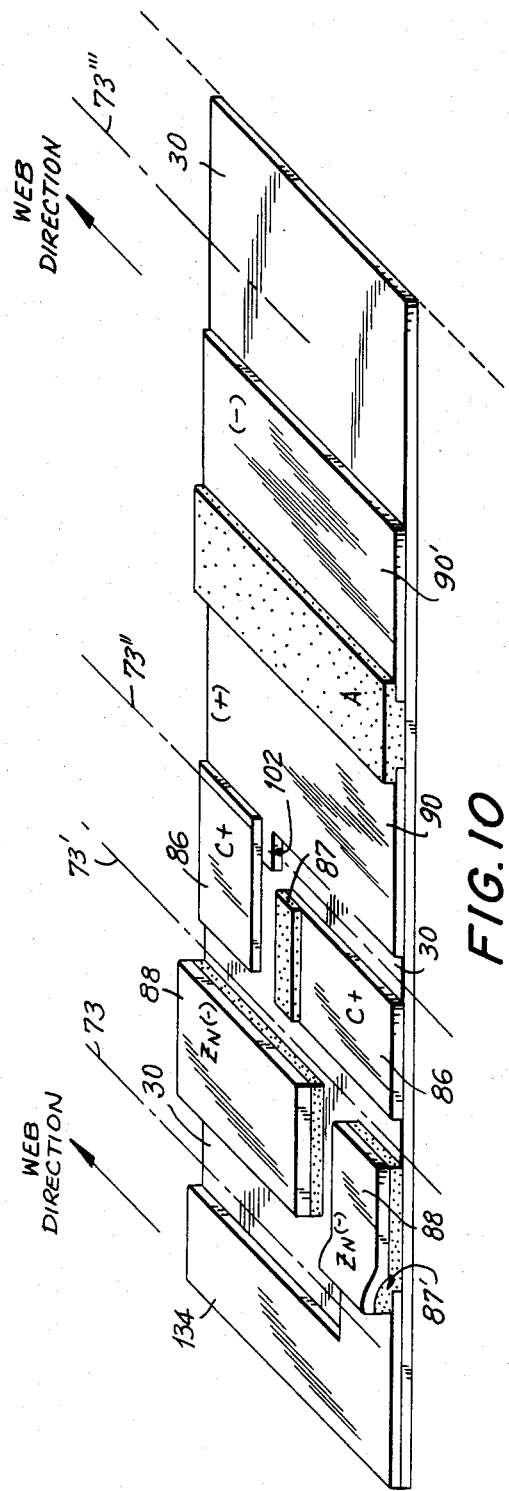
FIG. 10 illustrates an endless such substrate fed from rolled stock material upon which is provided thin sheet electrodes for the flat batteries and other rolled, layered materials for forming the power-source sub-assembly shown in FIG. 9.

As one 48' of the two disposed release liners can be further discarded in production, it can be considered optional, bearing in mind that the gel reservoirs and dams are viscous and retain their shape, and may even be further supported by a reinforcing web 62. FIG. 7 simply differs in that a semi-permeable membrane 64 is provided between the two sub-assemblies so that upon assembly, drug reservoirs are formed with areas or zones of different drug concentration or composition. Such a type of drug reservoir is noted to have significant advantages during operation of the transdermal device. Note that appropriate seals 47 can be provided along the semi-permeable membranes at the edges where each reservoir ends by means of heat or by other means to collapse the voids and seal the semipermeable membrane in those areas 47 where the seals are necessary. Alternately, silicone dams could also be used as seals between zones of semi-permeable materials. In addition, the semi-permeable materials may be preimpregnated with drugs or other chemicals which might be employed. These sub-assemblies of FIGS. 4–7 will now be shown and described as assembled onto the sub-assembly of FIG. 10. For purposes of disposability of the drug reservoirs, these sub-assemblies (FIGS. 4–7) are disposable and like replacements may be used to replenish the drug supply.

The disposable drug applicator 70 shown in FIG. 8 comprises an optionally replaceable drug reservoir sub-assembly 72 (any one of FIGS. 4–7) and a further sub-assembly 74 for the power means and electrical conditioning means which assemblies are secured together by suitable conductive adhesives. Sub-assembly 74 comprised essentially of battery 20 and current conditioning means 22 and associated reservoir conductors 24, 24' as best shown in FIG. 2. The electrical circuit running between the drug reservoirs and through the skin is a loop similar to that of FIG. 2, the only difference being the permanent nature of the battery and current/electrical conditioning means in the applicator structure rather than the reusable nature of the FIG. 2 embodiment. However, here just the drug reservoir sub-assembly 72 may be replaced where required.

Figure 8A:
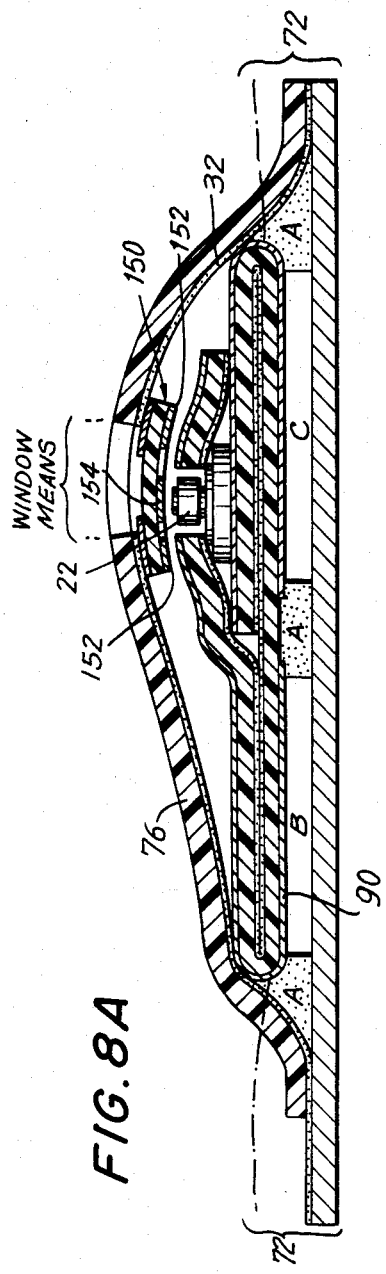
FIG. 8A is a cross-sectional view similar to that shown in FIG. 8, but illustrating an alternate drug applicator construction in which the outer conformal cover has window means through which current induced color changes or other visual feedback information can be viewed for verification of status of the drug delivery system, such as drug delivery taking place or having been terminated.

In FIG. 8A, the cover means 76 is suitably provided with window means, as is shown, which allows the status of the drug applicator to be observed. Such indicator means which is observed through the window means is more particularly described in my earlier filed U.S. patent application, Ser. No. 660,192, filed Oct. 12, 1984. As shown in FIG. 8A, the indicator means 150 is electrically in series with the current conditioning means 22 and conductive surface 90 which powers drug reservoir B. The connections of said indicator means 150 to the current conditioning means 90 and the conductive surface are achieved by means of a suitable flexible conductive adhesive, as is shown at the contact joints 152 and 154.

FIG. 9 represents a like kind of disposable drug applicator 80 having an optionally replaceable drug reservoir sub-assembly 72, as illustrated in FIGS. 8–8A, and a power source or flat layered battery, as as well as electrical or current conditioning means 84 sub-assembly which are secured together by suitable conductive adhesives. In this modification, the battery embodies sheet electrodes such as carbon (+) reference number 86 and zinc (−), reference number 88 and the drug reservoir electrodes 90, 90', which also are thin and flat. The battery electrodes 86, 88 are adhesively connected to a plastic substrate 30. The webbed material in production is preferably folded along the illustrated longitudinal fold lines, 73, 73', 73", 73''' (and others as may be required depending upon the required number of folds) cut transversely to a predetermined size. One carbon electrode 86 which is connected to the drug reservoir electrode 90 forms a battery with the large zinc electrode 88. The carbon electrode 86 which is connected to electrode 90 could be made as one unitary element. This large zinc electrode 88 is electrically connected to the other carbon electrode 86 by means of the conductive adhesive strip 87 (FIG. 10) at one end thereof, and thus forms a second battery, in series with the first battery, in conjunction with the small zinc electrode 88 which is likewise electrically connected to conductive surface 134 at 87' or simply with a conductive adhesive strip similar to 87.

It will be apparent to those skilled in the art that most or all of the battery components and connections within the applicator constructions of the invention could be applied by silk screen or rotogravure printing or, printed, die cut and stripped at high speed on standard roll label equipment.

A suitable current or other electronic conditioning means 84 is secured by a conductive adhesive 130 to one of the drug electrode conductive surfaces 90' having a flexible plastic substrate 30 and is also electrically connected to one of the battery electrodes, shown at 100 by means of an optional conductive indicator 150'. Optionally, a window means, such as a transparent area 156 of the cover 12 or an opening in said cover allows the viewing of an optional indicator 150'. In such case, the indicator 150' replaces the conductive connector. The last battery electrode, shown at 88 is electrically connected to the other drug electrode conductive surface 90 to form a complete electrical loop between the two drug reservoirs and through the skin. A suitable battery electrode element 131 impregnated with a gelled battery electrolyte is inserted between the carbon and zinc electrodes prior to folding, and the peripheries of the battery compartments are suitably sealed at 132 to prevent electrolyte leakage. In this modification, the drug reservoirs are also optionally removable if desired, as was shown in FIGS. 8–8A. It should also be apparent that in this modification, some adhesives employed may also be conductive while in other instances it is inherent that the adhesive has no other function than to secure together objects so it need not necessarily be conductive and in some cases it must not be conductive or a short circuit would occur. Also, the voltage of the battery will determine the numbers of carbon and zinc electrodes required, and such voltage can vary depending upon the applications. Although only carbon/zinc batteries are illustrated, other type battery cells could be made in a similar manner.

It will be apparent to those skilled in the art that various combinations of the previously described stages of applicator constructions can be embodied within one drug applicator device. For example, the function of the substrate 48' of FIGS. 6 or 7 could be provided by the electrode area 90, 90' of FIG. 10 in which case the addition of the second drug reservoir with its substrate (release liner 48) completes the product. It should also be evident that the construction shown in FIGS. 6 or 7 describes the replaceable drug reservoir which is employed by the end user (patient, nurse or doctor) by peeling off the release liner 48, applying the drug reservoir to the area 90, 90' of power supply applicator construction which results in the device shown in FIG. 9 which then could be applied on the human skin after peeling off the release liner 48. In this particular construction, it is envisioned that the battery life will be sufficient for the use of the applicator of FIG. 9 with a predetermined number of "refills" (similar to FIGS. 6 or 7) when marketed together in kit form. The same would hold true for all the other alternate constructions and embodiments of the invention. The power supply and the current regulating or electronic conditioning means is designed to perform only for a predetermined number of "refills" so as to quarantee medical supervision for each set of treatments (kit).

A current limiting resistor, in series with the battery can be manufactured by controlling the resistance of the conductive surfaces. Thus, such use would make the device fail safe and could provide current regulation in addition to or instead of solid state conditioning means 22 of FIG. 8. Therefore, if the current conditioning means 22 of FIG. 8 short circuits this resistor will limit the current to a safe value or level.

Although the present invention has been described in some detail by way of illustration and example for purposes of clarity and understanding, it will, of course be understood that various changes and modifications may be made in the form, details, and arrangements of the parts without departing from the scope of the invention as set forth in the following claims.

I claim:
1. A method of manufacturing a transdermal drug applicator which is adapted to be electrically activated, comprising the steps of:
    (a) applying conductive coated areas to the first surface of flexible, non-conductive substrate having first and second surfaces for use in said drug applicator, said coated areas and said substrate forming a one-piece member;
    (b) folding by about 180 degree portions of said one-piece member with said conductive coated areas so as to form folded top side and bottom side portions and to provide electrical conductors leading between said top side and bottom side portions;
    (c) applying at least one occlusive adhesive dam to the surface of another substrate containing thereon a coated release agent;
    (d) adding at least one drug resrvoir to said surface of said another substrate adjacent to said dam;
    (e) joining said at least one drug reservoir to a portion of at least one of said coated areas of said electrical conductors;
    (f) joining together in registration said bottom side of said one-piece member and said another substrate to form a sandwiched construction in which said at least one drug reservoir and said occlusive dam are contained between bottom side of said one-piece member and said another substrate;
    (g) applying a conformal cover having an adhesive coated surface over said second side of said flexible substrate of said folded one-piece member so as to enclose and protect said transdermal drug applicator.

2. The method of manufacturing a transdermal drug applicator which is adapted to be electrically activated according to claim 1, further comprising the step of applying an adhesive coating to said second surface of said flexible substrate.

3. The method of manufacturing a transdermal drug applicator which is adapt to be electrically activated according to claim 1, wherein at least one of conductive coated areas comprises carbon powder.

4. The method of manufacturing a transdermal drug applicator which is electrically activated according to claim 3, wherein said carbon powder contains a depolarizing agent.

5. The method of manufacturing a transdermal drug applicator which is electrically activated according to claim 3, wherein at least one of said conductive coated areas comprises a noble metal.

6. The method of manufacturing a transdermal drug applicator which is adapted to be electrically activated according to claim 1, further comprising the steps of adding a battery having terminals; extending one of said conductive coated areas to one terminal of said battery; extending the other terminal of said battery to another of said coated areas; and of electrically connecting said another said coated area so as to form an electrical circuit when said applicator is applied to the skin.

7. The method of manufacturing a transdermal drug applicator which is adapted to be electrically activated according to claim 6, further comprising the step of forming a plurality of negative and positive battery electrodes on said plastic substrate so as to form a plurality of battery cells; and electrically connecting the last negative and positive battery terminals to conductive surfaces on said plastic substrate.

8. The method of manufacturing a transdermal drug applicator which is adapted to be electrically activated according to claim 7, further comprising the step of interconnecting said positive and negative terminals of said battery cells in series by means of a conductive adhesive.

9. The method of manufacturing a transdermal drug applicator which is adapted to be electrically activated according to claim 8, further comprising the step of folding said flexible substrate along a plurality of fold lines so as to form said plurality of battery cells, and placing in between the terminals of each said cell a gelled battery electrolyte impregnated thermoplastic separator, and heat sealing the periphery of said cells.

10. The method of manufacturing a transdermal drug applicator which is adapted to be electrically activated according to claim 9, further comprising the step of adding an electronic current conditioning means in series with said battery on the positive terminal side of said battery.

11. The method of manufacturing a transdermal drug applicator which is adapted to be electrically activated according to claim 10, wherein all of the electrical connections within said drug applicator are made by the use of conductive flexible adhesives.

12. A method for making a replaceable disposable drug reservoir for a transdermal drug applicator adapted to be electrically powered, comprising the steps of:
   a. providing a release coated substrate;
   b. depositing on said substrate a plurality of occlusive adhesive dams made of a nonconductive material impervious to fluids to define a plurality of drug reservoir compartments;
   c. laminating an open cell foam material to said substrate over said occlusive adhesive dams so as to cause said nonconductive material to penetrate and fill the full thickness of said open cell foam; and
   d. filling said plurality of drug reservoir compartments with various gelled drug mixtures.

13. The method of manufacturing a transdermal drug applicator according to claim 12, further comprising the step of laminating together said replaceable drug reservoir with another drug reservoir, the lamination comprising a reinforcing scrim between the two drug reservoir layers.

14. The method of manufacturing a transdermal drug applicator, according to claim 12, further comprising the step of laminating together said replaceable drug reservoir with another drug reservoir, the lamination comprising a semipermeable membrane between the two drug reservoir layers.

15. The method of manufacturing a transdermal drug applicator which is adapted to be electrically activated according to claim 6, further including the steps of adding another drug reservoir to said surface of said another substrate with said dam separating said another drug reservoir from said drug reservoir; and joining said another drug reservoir to a portion of another of said coated areas so as to form said electrical circuit.

16. The method of manufacturing a transdermal drug applicator which is adapted to be electrically activated according to claim 6, further including the steps of forming an aperture in said conformal cover so as to make a well area adjacent to said coated area and said another coated area at said topside of said flexible member; and wherein said battery is a reusable battery adapted to be removably placed in said well area.

17. The method of manufacturing a transdermal drug applicator which is adapted to be electrically activated according to claim 16, wherein said reusable battery is a disc battery having terminals on opposite sides thereof.

18. The method of manufacturing a transdermal drug applicator which is adapted to be electrically activated according to claim 16, further including the step of adding timing and programmable control means with said reusable battery so as to make a reusable power and control unit adapted to be removably placed in said well of said applicator.

19. The method of manufacturing a transdermal drug applicator which is adapted to be electrically activated according to claim 6, wherein said battery includes a pair of positive and negative sheet electrodes.

20. The method of manufacturing a transdermal drug applicator which is adapted to be electrically activated according to claim 19, wherein said pair of electrodes is a plurality of electrodes forming a plurality of battery cells connected in series.

21. The method of manufacturing a transdermal drug applicator which is adapted to be electrically activated according to claim 19, wherein said positive and negative electrodes are zinc and carbon electrodes, respectively.

22. The method of manufacturing a transdermal drug applicator which is adapted to be electrically activated according to claim 6, wherein said at least one drug reservoir is on said one terminal of said battery and said another drug reservoir is on said other terminal of said battery, and wherein said at least one drug reservoir is a plurality of drug reservoirs and said another drug reservoir is a plurality of drug reservoirs.

23. The method of manufacturing a transdermal drug applicator which is adapted to be electrically activated according to claim 22, wherein said drug reservoirs include gels.

24. The method of manufacturing a transdermal drug applicator which is adapted to be electrically activated according to claim 23, wherein said gels are reinforced by scrims.

25. The method of manufacturing a transdermal drug applicator which is adapted to be electrically activated according to claim 23, wherein said drug reservoirs include open cell foam material impregnated with said gels.

26. The method of manufacturing a transdermal drug applicator which is adapted to be electrically activated according to claim 22, further including a semi-permeable membrane positioned in juxtaposition to said drug reservoirs, said semi-permeable membrane having seals corresponding to said dam so as define particular drug zones.

27. The method of manufacturing a transdermal drug applicator which is adapted to be electrically activated according to claim 26, wherein said drug zones containing drugs of different concentrations.

28. The method of manufacturing a transdermal drug applicator which is adapted to be electrically activated according to claim 26, wherein said drug zones contain drugs of different compositions.

29. A method of manufacturing a transdermal drug applicator which is electrically activated, comprising the steps of:
   a. applying conductive coated areas to one surface of a plastic substrate for use in said drug applicator;
   b. folding by about 180° portions of said conductive coated areas so as to provide electrical conductors leading to the other surface side of the drug applicator plastic substrate;
   c. applying at least one occlusive adhesive dam to a surface of another substrate containing thereon a coated release agent;
   d. adding at least one drug reservoir to said surface of said another substrate in areas not occupied by said occlusive adhesive dam;
   e. applying at least one drug reservoir to a portion of at least one of said electrical conductors;
   f. joining together in registration said plastic substrate and said another substrate to form a sandwiched construction in which said drug reservoirs and said occlusive adhesive dam are contained between said two substrates; and
   g. applying a conformal cover having an adhesive coated surface over the folded plastic substrate so as to enclose and protect said transdermal drug applicator.

30. The method of manufacturing a transdermal drug applicator which is electrically activated according to claim 29, further comprising the step of applying an adhesive coating to the opposite surface of said plastic substrate.

31. The method of manufacturing a transdermal drug applicator according to claim 1 or 29, wherein said another substrate is a release liner of said drug applicator.

32. The method of manufacturing a transdermal drug applicator according to claim 1 or 29, wherein said at least one drug reservoir having a scrim member so as to at least provide reinforcing of drug reservoir.

* * * * *